US00PP29899P2

(12) United States Plant Patent
Horvath

(10) Patent No.: US PP29,899 P2
(45) Date of Patent: Nov. 27, 2018

(54) ***STACHYS* PLANT NAMED 'SUMMER CRUSH'**

(50) Latin Name: ***Stachys* hybrid**
Varietal Denomination: Summer Crush

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 15/530,281

(22) Filed: Dec. 20, 2016

(51) Int. Cl.
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt

(57) ABSTRACT

A new, distinct *Stachys* plant as shown and described, characterized by the combination of lighter pink flowers and flower clusters.

1 Drawing Sheet

Figure 1:
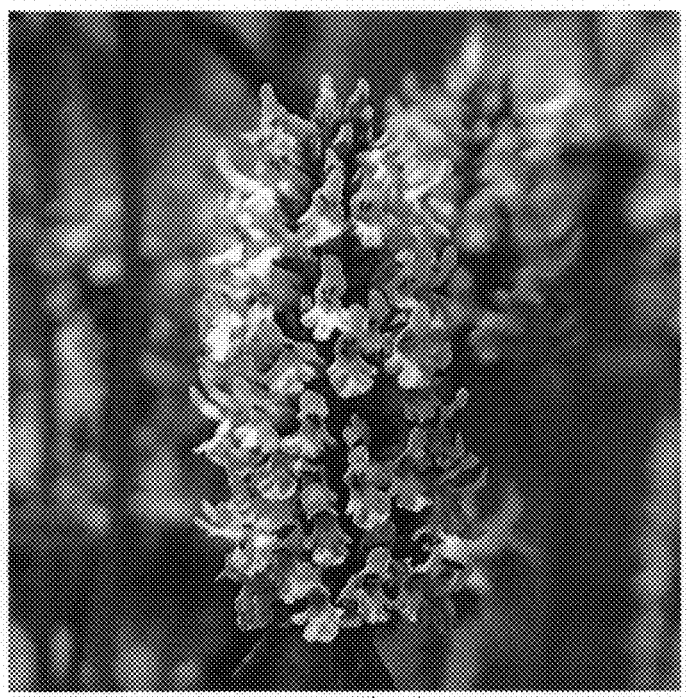

Latin name: *Stachys* hybrid.
Cultivar name: 'Summer Crush'.

BACKGROUND OF THE INVENTION

The present invention relates to a new and distinct hybrid of *Stachys* plant named 'Summer Crush' characterized by the combination of lighter pink flowers and flower clusters compared to the seed parent. The new *Stachys* was raised as a seedling from open pollinated seed sown from the seed parent, *Stachys* 'Pink Cotton Candy', U.S. Pat. No. 21,436, patented, in Hebron, Ill. in 2009. The selection of the new plant was due to its' long, lighter pink flower clusters and taller habit, compared to the seed parent. Initial asexual reproduction has taken place at a nursery in Hebron, Ill. since 2010 by means of division, and vegetative cuttings. The new *Stachys* has shown to be stable and identical in reproduction to the parent after rooting over 500 plants from 2010 to 2016. No plants of the new *Stachys* have been sold in this country, or anywhere in the world, prior to the filing of this application, nor has any disclosure of the new plant been made prior to the filing of this application with the exception of that which was disclosed within one year of filing of this application and was either derived directly or indirectly for the inventor.

SUMMARY OF THE INVENTION

The new *Stachys* plant named 'Summer Crush', characterized by longer light pink flowers and flower clusters compared to the seed parent have been observed to be unique and stable. For purpose of comparison the new plant will be referred to as 'Summer Crush'.

Plants of 'Summer Crush' can be compared to the plant of *Stachys* 'Hummelo', not patented. 1. The 'Summer Crush' plant is taller growing to 90 cm while *Stachys* 'Hummelo' grows to 40 cm. 2. The 'Summer Crush' plant has a bi-color flower color of N74 C with some lighter pink areas 75 C, while *Stachys* 'Hummelo' has a flower color of 77 A.

Plants of 'Summer Crush' can also be compared to the seed parent's pink flowered *Stachys* 'Pink Cotton Candy' U.S. Pat. No. 21,436, patented. 1. The 'Summer Crush' plant is taller growing to 90 cm while *Stachys* 'Pink Cotton Candy' grows to 47-50 cm. 2. The 'Summer Crush' plant has a bi-color flower of N74 C with some lighter pink areas 75 C, while *Stachys* 'Pink Cotton Candy' has a bi-color flower of N66 B and between 62 A and B.

DESCRIPTION OF PHOTOGRAPHS

Plants pictured in the drawing were grown for two years in a 3 gallon pot.

FIG. 1. Close up of the flower.

Figure 2:
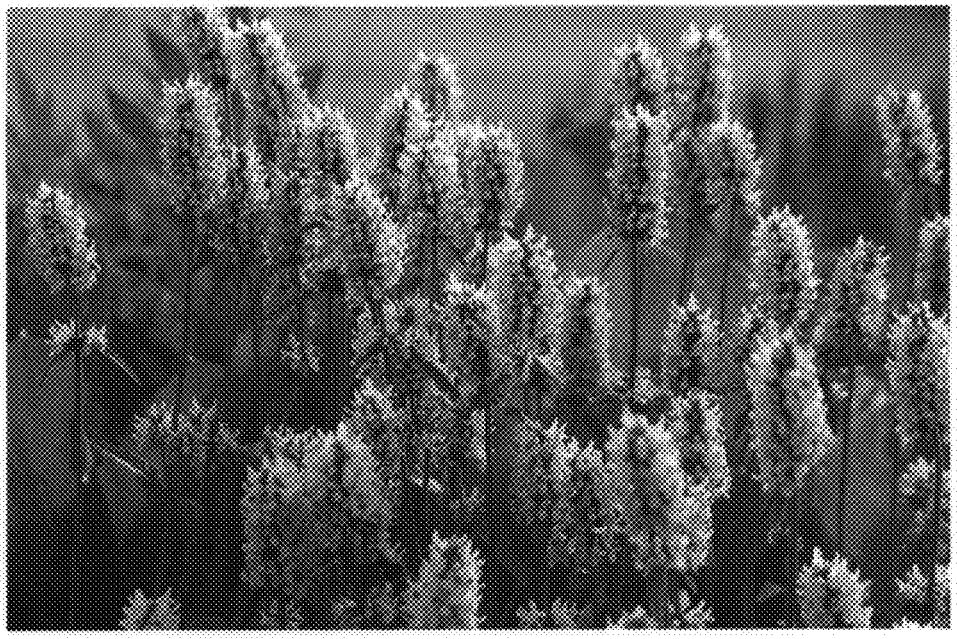

FIG. 2. A group of potted plants.

DETAILED BOTANICAL DESCRIPTION

In the following description, color references are made to The Royal Horticultural Society Colour Chart (2001). Plants used for the description were grown for two years. Measurements and numerical values represent averages of typical plants.

PLANT

Botanical classification: *Stachys* hybrid.
Form: Globular shape.
Height: 90 cm from soil to top of flowers; 50 cm wide.
Growth: Herbaceous perennial, broad upright, moderate vigor.
*Roots*.—Fine, compact, dense, freely branching, white.
Foliage:
*Arrangement*.—Opposite.
*Number of leaves per stem*.—4-8, 2 pairs per node. Nodes per stem. — 2-4.
*Size of leaf*.—Length: 13 cm on average, shorter at tops of stems. Width: 7 cm.
*Shape of leaf*.—Oval.
*Shape of tip*.—Obtuse.
*Shape of base*.—Sagittate.
*Texture*.—Rugose.
*Pubescence*.—Very dense rugose hairs, light green-white, less than 1-2 mm long on underside of main vein.

*Margin type*.—Dentate.
*Color*.—Young and Mature leaves: Upper surface: 137 B. Lower surface: close to 148 B.
*Petioles*.—Length: Up to 29 mm. Diameter: 3 mm, 8 mm at base. Color: Between 145 B and C.
*Veins*.—Pattern: Pinnate. Color: Upper surface: close to 137 B. Lower surface: 145 B and C.

Durability: Highly durable to stresses; when crushed, foliage spreads typical odor.

Response time to flower: About 10 months when grown in the containers.

FLOWER

Natural flowering season: Continuous from June into July.

Inflorescence type and habit: Branched, terminal verticillaster, labiate, no fragrance, flower lasts about three weeks on plant, self-cleaning.

Rate of flower opening: About 50-75% of flowers open at once, all flowers open in about 4 weeks.

Number of flowers: About 75 per spike; about 40 stems, 3000 flowers per plant.

Inflorescence size:
*Diameter*.—5 cm.
*Height*.—9 cm.
*Form*.—Quadrangular, strong.
*Pubescence*.—Densely covered with short grayish white hairs, about 1-2 mm long, more so on the bottom half of the stem.
*Branching*.—Yes, 2-4 nodes with a pair of leaves and a pair of inflorescences.
*Internode length*.—Ranges between 25 and 30 cm.
*Quantity*.—About 40 flowering lateral stems.

Peduncle:
*Length*.—22 cm.
*Diameter*.—2 mm.
*Color*.—Mostly N74 C with some lighter pink areas 75 C.
*Orientation*.—Upright.
*Strength*.—Strong.

Corolla:
*Petal arrangement*.—Labiate with one upper lip and one 3-lobed lower lips having one main lobe and two smaller side lobes.
*Overall size*.—10 mm high; 6 mm wide.
*Margin*.—Entire upper lip; 3-lobed lower lip.
*Tip shape*.—Emarginate upper lip; rounded lower lip.
*Length*.—Average upper lip: 7 mm; average lower lip: 6 mm.
*Width*.—Average upper lip: 4 mm; average lower lip: 5 mm.
*Petal quantity*.—2, fused at base.
*Petal apex shape*.—Upper lip; broad elliptic; folded; lower lip spathulate.
*Texture*.—Glabrous.
*Aspect*.—Drooping.
*Petaloids*.—None.

Color:
*Petals*.—When opening and fully open: Upper surface: Mostly N74 C with lighter pink areas 75 C. Lower surface: N74 C with lighter pink areas 75 C.

Bud:
*Shape*.—Obovate.
*Length*.—12 mm.
*Diameter*.—4 mm.
*Color*.—75 C.

Calyx:
*Arrangement*.—5 sepals fused into a tube at 90% of the length; 3 upper sepals fused nearly at the tips; 2 lower sepals fused nearly at the tips.
*Height*.—7 mm.
*Diameter*.—4 mm.
*Shape*.—Tubular.
*Sepals*.—Shape: Elliptic with acute tip and crenate base. Size: Average 7 mm long; 1-2 mm wide. Margin: Entire. Texture: Grayish hairs; less than 0.2 mm long. Color: Outer surface: N79 A at the top half and green 145 C at the base. Inner surface: from the tips down N79 A to green 145 D at the base. Bracts: 2 bracts under each whorl of flowers; deltoid shape with apiculate tip; upper surface 145 C lower surface 145 C with a N77 C spot or streaks.
*Odor*.—Present in petals and sepals.

REPRODUCTIVE ORGANS

Stamens:
*Number*.—4.
*Filament length*.—4 mm.
*Anthers*.—Shape: Basifixed, elliptic. Length: 0.05 mm. Color: White.
*Pollen*.—Color: white; too little to determine color. Amount Very low.

Pistil:
*Number*.—One.
*Length*.—12 mm.
*Style*.—Length: 12 mm. Color: N155 A at the top half fading to white at the base.
*Stigma*.—Shape: Cleft (2 parted). Color: N155 A. Ovary color: initially green close to 145 B.

Seeds and fruits: Yes brown and round 0.05 mm long and 0.05 mm wide, color 200 B.

Disease/pest resistance: No unusual susceptibility to diseases or pests has been noted to date.

Temperature tolerance: Tolerate to heat at least up to 30° C. and cool at least down to −28.9° C. USDA Zone 5.

I claim:

1. A new, distinct *Stachys* plant as shown and described, characterized by the combination of lighter pink flowers and flower clusters compared to the seed parent.

* * * * *